(12) United States Patent
Larsson

(10) Patent No.: US 9,408,755 B2
(45) Date of Patent: Aug. 9, 2016

(54) WOUND DRAINAGE DRESSING

(75) Inventor: Michael Larsson, Zug (CH)

(73) Assignee: MEDELA HOLDING AG, Baar (CH)

( * ) Notice: Subject to any disclaimer, the term of this patent is extended or adjusted under 35 U.S.C. 154(b) by 294 days.

(21) Appl. No.: 12/741,651

(22) PCT Filed: Nov. 4, 2008

(86) PCT No.: PCT/CH2008/000466
§ 371 (c)(1),
(2), (4) Date: May 6, 2010

(87) PCT Pub. No.: WO2009/062327
PCT Pub. Date: May 22, 2009

(65) Prior Publication Data
US 2010/0262091 A1    Oct. 14, 2010

(30) Foreign Application Priority Data

Nov. 13, 2007    (CH) ........................................ 1755/07

(51) Int. Cl.
*A61M 1/00* (2006.01)
*A61F 13/36* (2006.01)
(Continued)

(52) U.S. Cl.
CPC ........... *A61F 13/36* (2013.01); *A61F 13/00068* (2013.01); *A61M 1/0088* (2013.01); *A61F 2013/0054* (2013.01); *A61F 2013/00174* (2013.01); *A61F 2013/00182* (2013.01); *A61F 2013/00412* (2013.01); *A61F 2013/00536* (2013.01); *A61F 2013/00846* (2013.01)

(58) Field of Classification Search
CPC ......... A61M 1/00; A61M 5/178; A61M 5/00; A61M 5/32; A61M 35/00; A61F 13/00

USPC .......................................... 604/300, 304, 305
See application file for complete search history.

(56) References Cited

U.S. PATENT DOCUMENTS 5,653,699 A    8/1997    Reed et al.
5,989,478 A    11/1999    Ouellette et al.
(Continued)

FOREIGN PATENT DOCUMENTS

DE        10055902       6/2001
DE      102005007016     8/2006
(Continued)

OTHER PUBLICATIONS

International Preliminary Report on Patentability for corresponding PCT Patent Application No. PCT/CH2008/000466.
(Continued)

*Primary Examiner* — Tatyana Zalukaeva
*Assistant Examiner* — Ilya Treyger
(74) *Attorney, Agent, or Firm* — McDonnell Boehnen Hulbert & Berghoff LLP

(57) ABSTRACT

The invention relates to a wound drainage covering for covering, by means of low pressure, a wound that is to be treated. The covering comprises at least two layers that are superimposed. A first layer that is applied on the side of the wound is made of a functional textile material and second layer that is arranged thereon is dimensionally stable and permeable to liquid. The wound drainage covering has a simple design and due to the functional first layer, is effective and ensures, due to the dimensionally stable second layer, an optimal removal of wound secretion.

6 Claims, 2 Drawing Sheets

(51) Int. Cl.
*A61F 13/00* (2006.01)
*A61M 5/178* (2006.01)
*A61M 5/00* (2006.01)
*A61M 5/32* (2006.01)
*A61M 35/00* (2006.01)

(56) References Cited

U.S. PATENT DOCUMENTS

| | | |
|---|---|---|
| 6,077,526 A | 6/2000 | Scully et al. |
| 6,685,681 B2 * | 2/2004 | Lockwood et al. .......... 604/305 |
| 7,070,584 B2 | 7/2006 | Johnson et al. |
| 7,198,046 B1 * | 4/2007 | Argenta ................ A61M 1/005 128/897 |
| 7,759,537 B2 * | 7/2010 | Bishop et al. .................... 602/43 |
| 7,815,616 B2 * | 10/2010 | Boehringer et al. .......... 604/313 |
| 2002/0065494 A1 | 5/2002 | Lockwood et al. |
| 2004/0073151 A1 | 4/2004 | Weston |
| 2004/0260258 A1 * | 12/2004 | Hall ................... A61F 13/4702 604/367 |
| 2005/0004536 A1 * | 1/2005 | Opie et al. .................... 604/317 |
| 2005/0137539 A1 | 6/2005 | Biggie et al. |
| 2006/0079852 A1 | 4/2006 | Bubb et al. |
| 2007/0066946 A1 * | 3/2007 | Haggstrom et al. .......... 604/313 |
| 2008/0167593 A1 * | 7/2008 | Fleischmann .................. 602/48 |

FOREIGN PATENT DOCUMENTS

| | | |
|---|---|---|
| EP | 0099758 | 2/1984 |
| EP | 0620720 | 10/1994 |
| EP | 1284777 | 2/2003 |
| WO | 03/086232 | 10/2003 |
| WO | 2004/060412 | 7/2004 |
| WO | 2006/048240 | 5/2006 |
| WO | 2006/052839 | 5/2006 |
| WO | 2006/056294 | 6/2006 |
| WO | 2007/030601 | 3/2007 |

OTHER PUBLICATIONS

International Search Report for corresponding international application No. PCT/CH2008/000466 dated Apr. 2, 2009.

* cited by examiner

WOUND DRAINAGE DRESSING

CROSS REFERENCE TO RELATED APPLICATIONS

This application claims priority to International Application Ser. No. PCT/CH2008/000466 filed Nov. 4, 2008, which claims priority to Swiss Patent Application No. 01755/07 filed Nov. 13, 2007, the contents of which are incorporated by reference herein in their entirety.

TECHNICAL FIELD

The invention relates to a wound drainage dressing.

PRIOR ART

It is known to treat large or poorly healing wounds using a vacuum drainage device. A cover, for example a film or a stiff cap, covers the wound, such that a wound space is obtained. A drainage hose is inserted into the wound space from outside and is connected to a vacuum pump in order to suck wound secretions out of the wound. In order to fill the wound space, and in particular to distribute the vacuum uniformly across the wound surface, a wound drainage dressing is placed on the wound. This wound drainage dressing is usually a foam insert with suitably configured pores. The foam insert usually also serves as an absorption body for the wound secretions and therefore has to be frequently changed. Corresponding wound drainage dressings are known, for example, from WO 2006/056294, U.S. Pat. No. 7,070,584, EP 1 284 777 and EP 0 620 720. A wound drainage dressing with a foam insert outside the airtight top sheet is described in WO 2006/052839.

However, these foam inserts have the disadvantage that, when a vacuum is applied, they collapse, or their pores at least block. As a result, a constant transport of fluid cannot be maintained. In the worst case, the transport of the wound secretions is even blocked.

WO 03/086232 further discloses a wound drainage dressing for placing on a wound that is to be treated by vacuum, with a layer which is placed on the surface of the wound and which has through-holes and channels for distribution of the vacuum, and with a top sheet which is arranged over the layer and which has an access opening for the vacuum hose. The wound dressing is stiff and incompressible. It is also transparent, such that the wound healing can be monitored. The wound drainage dressing can be impregnated with silver ions.

US 2002/0065494 discloses a similar wound drainage dressing, where a gauze is arranged over the top sheet and fills the wound cavity up to the height of the healthy skin. A film is arranged over this gauze and allows water vapor to escape from the cavity.

EP 0 099 758 discloses a wound dressing for use without drainage, in particular for use with electrical stimulation. This wound dressing is multilayered and has a semipermeable membrane, a permeable reinforcing layer made of a textile material, and a biodegradable, non-adhesive contact layer. The membrane controls the transfer of water vapor away from the wound. In U.S. Pat. No. 5,653,699 too, a wound dressing without drainage is described that is able to control the transfer of water vapor for the purpose of keeping the wound moist. Wound dressings with layers that transport a fluid into a next higher layer are also described, for example in U.S. Pat. No. 6,077,526 and WO 2004/060412.

U.S. Pat. No. 5,989,478 discloses a woven fabric, which is proposed as a top sheet for sanitary towels, diapers or wound dressings. The woven fabric is permeable to liquid and actively transports the liquid from one surface to the opposite surface, where the liquid can be delivered to a suction layer.

SUMMARY OF THE INVENTION

It is an object of the invention to create a wound drainage dressing that ensures optimal transport of wound secretions while being of simple construction.

The wound drainage dressing according to the invention, for placing on a wound that is to be treated by vacuum, has at least two layers arranged one on top of the other, wherein a first layer facing the wound is a functional textile material, and a second layer, arranged over the first layer, is dimensionally stable and permeable to liquid.

The functional textile material is preferably permeable to liquid at least in one direction and preferably has an anisotropic configuration.

This wound drainage dressing is suitable for use as an inlay in a wound, to which a vacuum is applied. Such wound drainage arrangements are suitable for the healing of wounds in humans and animals.

The first layer and the second layer can be single-ply and be designed uniformly across the entire volume, or they can each be made from a composite material. The second layer is preferably wide-meshed or designed with large openings otherwise distributed across its surface or the entire volume, such that the applied vacuum can be distributed uniformly and the suction channels of the second layer cannot be blocked by wound secretions being sucked out.

Other advantageous embodiments are set forth in the dependent claims.

BRIEF DESCRIPTION OF THE DRAWINGS

The subject matter of the invention is explained below on the basis of a preferred illustrative embodiment and with reference to the attached drawings, in which.

DETAILED DESCRIPTION

Figure 1:
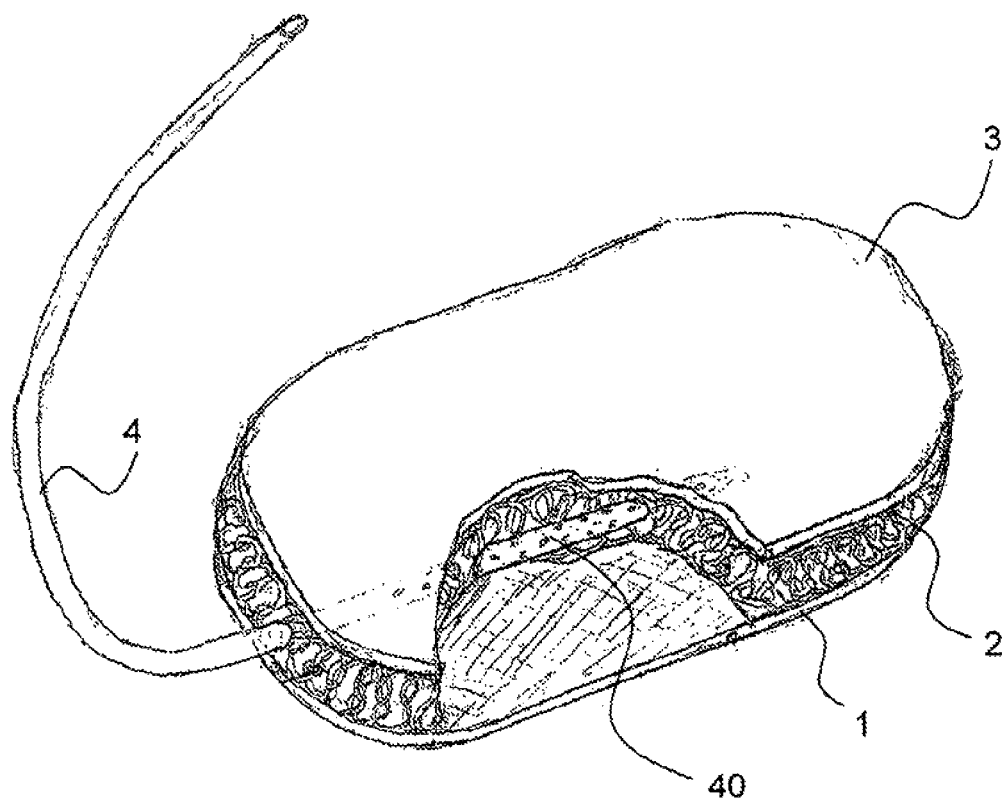
FIG. 1 shows a schematic representation of a wound drainage dressing according to the invention.
Figure 2:
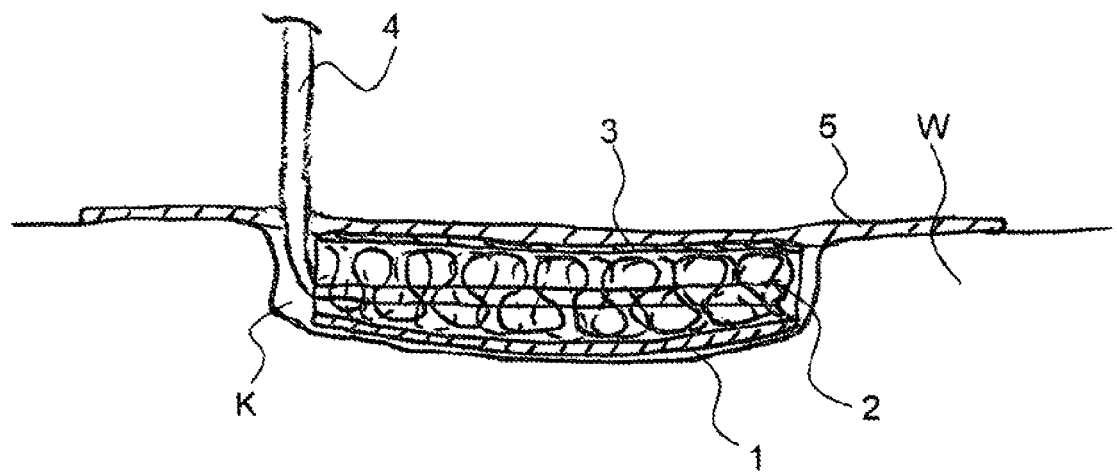
FIG. 2 shows the wound drainage dressing according to FIG. 1 in use in a wound.
Figure 3:
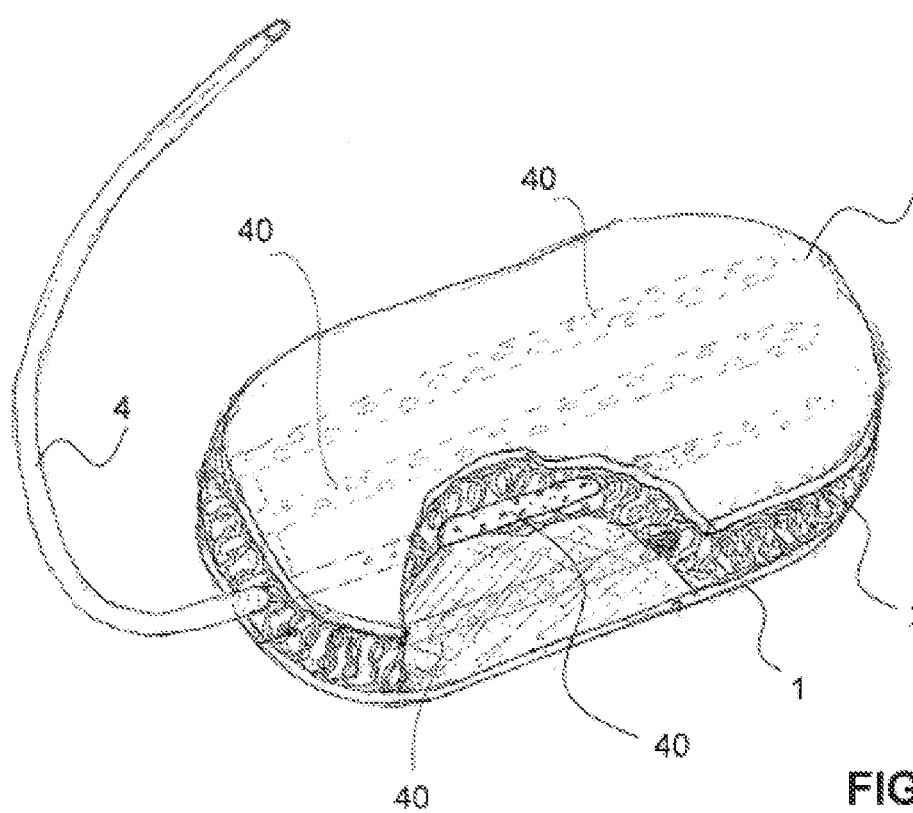
FIG. 3 shows the wound drainage dressing according to FIG. 1 including a plurality of distributor tubes.

FIG. 1 shows a preferred illustrative embodiment of the wound drainage dressing according to the invention or the filler according to the invention. As can be seen from FIG. 2, it is used for placing on a wound W and for inserting into a wound cavity K, wherein the wound drainage dressing is covered completely with an airtight cover 5, and the wound cavity K is thus sealed in an airtight manner. The cover 5 can be a rigid cap, a flexible film, or another cover means known from the prior art. The cover 5 is preferably self-adhesive, at least at the edges thereof, such that it can be affixed in an airtight manner to the healthy skin surrounding the patient's wound. However, it is also possible for the cover 5 not to be self-adhesive and for it to be secured by additional securing means, in particular adhesive strips.

A drainage hose 4 leads outward from the wound drainage dressing. This drainage hose 4 is connected to a vacuum pump, such that a vacuum can be generated in the cavity K, and the liquid present in the cavity K, in particular the wound secretions, can be sucked out. A vacuum of 50 mmHg to 220 mmHg is typically generated. In addition to the drainage hose 4, one or more supply lines can be routed through the cover 5 into the cavity K. Cleaning solutions, such as sodium chloride, or medicaments, for example zinc oxide, can be introduced into the wound cavity K through these supply lines.

As can be seen in FIG. 1, the wound drainage dressing according to the invention is foamless. It is composed of at least two layers or plies arranged one on top of the other, namely a first layer 1 facing the wound and made from a functional material, and a second layer 2, which is arranged over the first layer 1 and which is dimensionally stable or stiff and is permeable to liquid. As is shown in FIG. 1, a third layer 3 can additionally be present, which covers the second layer 2 and is designed as a liquid-impermeable top layer. It can be airtight but does not have to be.

The first layer 1 is made from a functional textile material. A textile material is understood here as a material that can be in the form of a woven fabric or knitted fabric, for example. A functional material is understood here as a material that is able to perform an active function, for example transporting liquid or dispensing medicaments. The materials known from the sports clothing industry are suitable in particular as the functional textile material.

The first layer is preferably flexible, in particular a flexible woven fabric. This first layer 1 can be configured as a single ply. However, it preferably has several plies with different functions. This first layer 1 preferably has a thickness of 0.1 mm to 5 mm. This first layer 1 is preferably self-supporting. It can be connected to the second layer 2, in which case it does not necessarily have to be self-supporting.

The functionality of the material can be of various types. In a preferred embodiment, this first layer 1 is configured in such a way that it can perform an active or automatic transport of liquid. That is to say, the wound liquid is transported away from the wound into the next higher layer, here the second layer 2, even without application of a vacuum. For this purpose, the first layer 1 preferably has capillaries. Materials of this kind are known from the prior art, for example for sports clothing, or, as was mentioned at the outset, for sanitary towels, diapers and bandages without drainage.

In another preferred embodiment, the first layer 1 is designed for delayed and/or precisely metered dispensing of active substances. It can, for example, dispense medicaments and/or be coated with silver ions. This functionality can be combined with the functionality of the automatic transport of liquid. Other functionalities of the kind known from the field of nanotechnology are likewise possible.

The second ply or layer 2 is relatively stiff or at least dimensionally stable. However, adaptation to irregularities in the wound is preferably possible. Dimensionally stable in this context is intended to signify that, when a vacuum is applied, this second layer 2 does not collapse, and its inner cavities or channels are not compressed, or they are compressed only to an insignificant extent. It is also permeable to liquid and is designed with sufficiently large inner openings to allow the wound secretions to be sucked out through this second layer 2, without this second layer 2 becoming blocked. These inner openings are preferably distributed uniformly across the entire surface of the second layer 2, such that the applied vacuum can be distributed uniformly on the surface of the first layer 1 and thus of the wound. The second layer 2 is preferably designed uniformly across the entire volume, i.e. the inner openings are distributed uniformly across the entire volume. However, it is also possible for the size, number and distribution of the openings in the area of the second layer 2 near the wound to be different than in the area of the second layer 2 directed away from the wound. This second layer is preferably composed of a single ply. However, it can also be configured with several plies, and the individual plies can be identical to or different than one another. Thus, for example, a ply of the second layer 2 near the wound can have larger openings or a greater number of openings than a ply directed away from the wound. The second layer 2 is preferably a wide-meshed woven fabric, a loose knitted fabric or a wire braid. It can, for example, be made from a plastic or from a metal. The thickness of the second layer 2 depends on the configuration and depth of the wound. The second layer 2 has in particular a thickness many times greater than the first layer 1.

The third layer 3 is impermeable to liquid and is preferably airtight. It is, for example, a simple woven fabric, a film or a coating, which is applied to the second layer 2, in particular affixed or welded thereto. This third layer 3 is preferably transparent, such that the flow of wound secretions or the flow of medicament in the second layer 2 can be monitored. The abovementioned cover 5 is preferably also transparent.

In this example, the drainage hose 4 is inserted laterally into the second layer 2 directly, i.e. without passing through the third layer 3. However, it can also pass through the third layer 3. Within the second layer, the drainage hose 4 merges into one or more distributor tubes 40, which have suction openings distributed about their circumference. The distributor tubes 40 can be formed integrally on the hose 4 or can be plugged to the latter. These distributor tubes 40 preferably extend approximately across the entire width and length of the second layer. It is also possible, however, to insert the drainage hose 4 approximately centrally into the second layer 2 or to have the latter end only in an edge area and continue no further into the second layer 2. The applied vacuum is distributed uniformly thanks to the presence of the large openings in the second layer 2.

The wound drainage dressing according to the invention is of simple construction, has a good mode of action thanks to the functional first layer, and ensures optimal transport of wound secretions thanks to the dimensionally stable second layer.

The invention claimed is:

1. A wound drainage dressing for placing on a wound that is to be treated by vacuum, wherein the wound drainage dressing is suitable for inserting a drainage hose into the wound from outside and for connecting this drainage hose to a vacuum pump in order to generate a vacuum in the wound and suck out the wound liquid present in the wound, wherein the wound drainage dressing has at least two layers arranged one on top of the other, wherein a first layer facing the wound is a textile material, and a second layer, arranged over the first layer, and made of a different material than the first layer, is dimensionally stable such that when the vacuum is applied to the wound, the second layer does not collapse, the second layer being permeable to liquid, and wherein the first layer is made from a functional textile material which has an anisotropic configuration and which performs active transport of liquid, the active transport of the first layer comprising the transport of wound liquid away from the wound into the second layer without application of the vacuum, the first layer having capillaries for the active transport of the liquid into the second layer, wherein a drainage hose is directly inserted laterally into the second layer without passing through the third layer, the drainage hose merging into distributor tubes which are arranged in the second layer, wherein the distributor tubes have a plurality of suction openings distributed about a circumference and wherein the distributor tubes extend approximately across the entire width and length of the second layer, and wherein the wound drainage dressing further comprises a third layer arranged over the second layer, the third layer being impermeable to liquid, the third layer further being transparent such that a flow of wound liquid in the second layer can be monitored.

2. The wound drainage dressing as claimed in claim 1, wherein the second layer is a woven fabric, a knitted fabric or a wire braid.

3. The wound drainage dressing as claimed in claim 1, wherein the material of the first layer is suitable for delayed or precisely metered dispensing of active substances, in particular of medicaments or silver ions.

4. The wound drainage dressing as claimed in claim 1, wherein the material of the first layer is a flexible woven fabric.

5. The wound drainage dressing as claimed in claim 1, wherein the second layer has a thickness greater than the first layer.

6. The wound drainage dressing as claimed in claim 1, wherein said wound drainage dressing is foamless.

\* \* \* \* \*